United States Patent
Mccann et al.

(10) Patent No.: US 11,759,121 B2
(45) Date of Patent: Sep. 19, 2023

(54) APPARATUS AND METHOD FOR ESTIMATING RESPIRATION RATE

(71) Applicant: CURRENT HEALTH LIMITED, Edinburgh (GB)

(72) Inventors: Christopher Thomas Mccann, Edinburgh (GB); Stewart William Whiting, Edinburgh (GB)

(73) Assignee: CURRENT HEALTH LIMITED, Edinburgh (GB)

(*) Notice: Subject to any disclaimer, the term of this patent is extended or adjusted under 35 U.S.C. 154(b) by 305 days.

(21) Appl. No.: 16/633,077

(22) PCT Filed: Nov. 27, 2018

(86) PCT No.: PCT/GB2018/053420
§ 371 (c)(1),
(2) Date: Jan. 22, 2020

(87) PCT Pub. No.: WO2019/106351
PCT Pub. Date: Jun. 6, 2019

(65) Prior Publication Data
US 2020/0163586 A1 May 28, 2020

(30) Foreign Application Priority Data

Nov. 28, 2017 (EP) .................................... 17204223

(51) Int. Cl.
*A61B 5/08* (2006.01)
*A61B 5/024* (2006.01)
(Continued)

(52) U.S. Cl.
CPC .......... *A61B 5/0816* (2013.01); *A61B 5/0295* (2013.01); *A61B 5/02416* (2013.01); *A61B 5/113* (2013.01); *A61B 5/6824* (2013.01)

(58) Field of Classification Search
CPC ... A61B 5/0816; A61B 5/02416; A61B 5/113; A61B 5/6824; A61B 5/0295; A61B 5/145
See application file for complete search history.

(56) References Cited

U.S. PATENT DOCUMENTS 5,497,769 A * 3/1996 Gratton ................ A61B 5/0059
356/41
9,526,431 B2† 12/2016 Zakharov
(Continued)

FOREIGN PATENT DOCUMENTS

| WO | 2015/171667 | 11/2015 |
| WO | 2017/220526 | 12/2017 |

OTHER PUBLICATIONS

Walter Karlen, et al., "Multiparameter Respiratory Rate Estimation From the Photoplethysmogram", IEEE Transactions on Biomedical Engineering, vol. 60, No. 7, Jul. 2013, 9 pages.
(Continued)

*Primary Examiner* — Kaylee R Wilson
*Assistant Examiner* — Abid A Mustansir
(74) *Attorney, Agent, or Firm* — Nixon & Vanderhye P.C.

(57) ABSTRACT

Monitoring apparatus for measuring the respiratory rate of a subject comprises an upper arm unit attached to a subject's upper arm in use and containing at least one movement sensor and a photoplethysmograph configured to monitor blood volume within the subject's upper arm while the upper arm unit is worn on the subjects upper arm. The output from the photoplethysmograph and movement sensor(s) are processed to calculate and output an estimate of the rate of respiration of the subject. Respiratory cycle induced variations in the photoplethysmograph signal and movement sensor signals can be independently determined and there is a greater confidence in the calculated respiratory rate when these independent calculations give consistent readings. If
(Continued)

there is insufficient confidence, no rate of respiration is displayed.

21 Claims, 11 Drawing Sheets

(51) Int. Cl.
*A61B 5/0295* (2006.01)
*A61B 5/113* (2006.01)
*A61B 5/00* (2006.01)

(56) References Cited

U.S. PATENT DOCUMENTS

| | | | |
|---|---|---|---|
| 2008/0081961 A1 | 4/2008 | Westbrook et al. | |
| 2008/0303660 A1 | 12/2008 | Lombardi | |
| 2010/0297978 A1 | 11/2010 | McClenny et al. | |
| 2010/0298650 A1 | 11/2010 | Moon et al. | |
| 2011/0054277 A1 | 3/2011 | Pinter et al. | |
| 2011/0066007 A1 | 3/2011 | Banet et al. | |
| 2012/0154157 A1 | 6/2012 | George | |
| 2012/0203077 A1 | 8/2012 | He et al. | |
| 2013/0116520 A1 | 5/2013 | Roham et al. | |
| 2013/0324816 A1* | 12/2013 | Bechtel | A61B 5/72 600/331 |
| 2013/0331058 A1 | 12/2013 | Harvey | |
| 2013/0338460 A1 | 12/2013 | He et al. | |
| 2014/0228657 A1 | 8/2014 | Palley et al. | |
| 2014/0276175 A1 | 9/2014 | Banet et al. | |
| 2015/0305632 A1 | 10/2015 | Najarian et al. | |
| 2015/0313484 A1 | 11/2015 | Burg et al. | |
| 2016/0007934 A1 | 1/2016 | Arnold et al. | |
| 2016/0007935 A1 | 1/2016 | Hernandez et al. | |
| 2016/0051205 A1 | 2/2016 | Al-Ali et al. | |
| 2017/0119314 A1* | 5/2017 | Just | A61B 5/6816 |
| 2019/0261890 A1* | 8/2019 | Li | A61B 5/0077 |
| 2019/0282180 A1† | 9/2019 | Babaeizadeh | |
| 2019/0357850 A1† | 11/2019 | Li | |

OTHER PUBLICATIONS

International Search Report and Written Opinion of PCT/GB2018/053420 dated Mar. 20, 2019, 10 pages.
International Preliminary Report on Patentability of PCT/GB2018/053420 dated Nov. 18, 2019, 6 pages.
Third Party Observations and Submission of Prior Art in the examination proceedings of European Patent Application No. 17204223.6 (8 pages).

\* cited by examiner
† cited by third party

APPARATUS AND METHOD FOR ESTIMATING RESPIRATION RATE

This application is the U.S. national phase of International Application No. PCT/GB2018/053420 filed Nov. 27, 2018 which designated the U.S. and claims priority to EP Application No. 17204223.6 filed Nov. 28, 2017, the entire contents of each of which are hereby incorporated by reference.

FIELD OF THE INVENTION

The present invention relates to the field of wearable devices for measuring the respiration rate of a subject (typically in addition to other physiological parameters).

BACKGROUND TO THE INVENTION

It is desirable to automatically measure the respiration rate of a human subject to facilitate medical monitoring over a period of time. It is known to provide respiratory rate monitoring devices for use in a clinical setting which measure the physical movement of the chest wall. However, such devices are readily detached and not practical for use with a patient who is moving, for example for monitoring patients outside of a clinical setting.

It is also known to determine respiration rate from the respiratory cycle induced variation in measurements made using a photoplethysmograph (PPG). Such devices are typically attached to a patient's digit (typically their thumb) in a clinical setting. It is known to provide wrist mounted devices with PPG attachments for a patient's thumb in order to provide an ambulatory device. However, these techniques are not accurate for long term monitoring of a subject, particularly a subject who is moving around, outside of a clinical environment, or who has vasoconstriction (e.g. whether due to a medical condition, or a medical treatment which they are receiving, or simply due to being cold).

Accordingly, the invention seeks to provide apparatus and method for monitoring the respiration rate of a human subject which are reliable and useful with patients who may move around.

SUMMARY OF THE INVENTION

According to a first aspect of the invention there is provided monitoring apparatus for measuring the respiratory rate of a subject, the monitoring apparatus comprising an upper arm unit configured for attachment to a subject's upper arm,
  the upper arm unit comprising at least one movement sensor and a photoplethysmograph configured to monitor blood volume within the subject's upper arm while the upper arm unit is worn on the subject's upper arm,
  at least one processor programmed to process both the output of the at least one movement sensor and the output of the photoplethysmograph to thereby calculate and output an estimate of the rate of respiration of the subject.

According to a second aspect of the invention there is provided a method of measuring the respiratory rate of a subject using an upper arm unit which is attached to a subject's upper arm,
  the upper arm unit comprising at least one movement sensor and a photoplethysmograph configured to monitor blood volume within the subject's upper arm while the upper arm unit is worn on the subject's upper arm,
  the method comprising processing both the output of the at least one movement sensor and the output of the photoplethysmograph to thereby calculate an estimate of the rate of respiration of the subject, and then outputting the calculated estimate of the rate of respiration of the subject.

We have found that it is surprisingly advantageous to provide a monitor which comprises an upper arm unit with both at least one movement sensor and a photoplethysmograph, and to process the measurements from both the at least one movement sensor and the photoplethysmograph to estimate respiratory rate because:
  a sufficiently sensitive movement sensor in an upper arm unit can, in at least some body postures, directly detect respiratory movement of the thorax;
  although the strength of the photoplethysmograph signal is typically weaker at the upper arm position than at a subject's finger, we have found that surprisingly, when a subject is moving, the quality of the signal is cleaner and more reliable than the signal measured at a finger;
  although the strength of the photoplethysmograph signal is typically weaker at the upper arm position than at a subject's finger, we have found that surprisingly the quality of the signal is cleaner than the signal measured at a finger when a subject is suffering from vasoconstriction.

Typically, the upper arm unit comprises a housing which includes the at least one movement sensor and the photoplethysmograph therein. Typically, the photoplethysmograph comprises one or more light sources (e.g. LEDs) and one or more light detectors (e.g. photodiodes) on or under a light transmitting surface of the casing. The housing may have an incurvate subject-facing surface, including the light transmitting surface, thereby increasing the contact area between the arm unit and the subject's arm. It may be that the radius of curvature of the subject-facing surface is between 200 mm and 400 mm, or more preferably between 250 mm and 350 mm, or more preferably between 290 mm and 310 mm.

The at least one movement sensor may comprise one or more accelerometers, for example a multi-axis (e.g. two axis or typically three axis) accelerometer. An accelerometer measures movement because the upper arm can only move a limited distance and so movement leads to acceleration and deceleration within a short time period.

Processing the output of the at least one movement sensor may comprise processing the output from one or more accelerometers to thereby detect movement. We have found it advantageous to measure acceleration along at least two, and preferably three, axes to maximise the chance of detecting movement given the range of postures which might be adopted by a patient (e.g. lying on one side or another, their front or back, sitting, walking, with their arm against their body or stretched away from their body).

The at least one movement sensor may comprise one or more gyroscopes, for example a multi-axis (e.g. two axis or typically three axis) gyroscope. Processing the output of the at least one movement sensor may comprise processing the output from one or more gyroscopes to thereby detect (rotational) movement. We have found it advantageous to measure a rate of rotation along at least two, and preferably three, axes to maximise the chance of detecting movement given the range of postures which might be adopted by a patient.

The said processing may comprise analysing whether the output from the photoplethysmograph meets one or more quality criteria.

The said processing may comprise analysing whether the output from the one or more movement sensors meets one or more quality criteria.

The said processing may comprise calculating at least one first (PPG-derived) estimate of the rate of respiration by determining the frequency of a respiratory cycle induced variation in the output of the photoplethysmograph, and may also comprise determining whether the said first estimate of the rate of respiration meets one or more accuracy criteria.

The said processing may comprise calculating at least one second (movement-derived) estimate of the rate of respiration by determining the frequency of a respiratory cycle induced variation in the output of the one or more movement sensors, and may also comprise determining whether the said second estimate of the rate of respiration meets one or more accuracy criteria.

The said processing may comprise both:
(a) calculating at least one first (PPG-derived) estimate of the rate of respiration by determining the frequency of a respiratory cycle induced variation in the output of the photoplethysmograph; and
(b) calculating at least one second (movement-derived) estimate of the rate of respiration by determining the frequency of a respiratory cycle induced variation in the output of the one or more movement sensors.

The said processing may comprise outputting (and the processor may output) a rate of respiration calculated from both at least one said first estimate and at least one said second estimate of the rate of respiration, optionally only if both the at least one said first estimate and the at least one said second estimate meet at least one similarity criterion.

The said processing may comprise outputting (and the processor may output) either:
(a) a first (PPG-derived) estimate of the rate of respiration calculated by determining the frequency of a respiratory cycle induced variation in the output of the photoplethysmograph; or
(b) a second (movement-derived) estimates of the rate of respiration calculated by determining the frequency of a respiratory cycle induced variation in the output of the one or more movement sensors,
typically in dependence on (i) whether the output of the photoplethysmograph meets one or more quality criteria and/or (ii) whether the first estimate meets one or more accuracy criteria; and also (iii) whether the output of the movement sensors meets one or more quality criteria and/or (iv) whether the second estimate meets one or more accuracy criteria.

That is to say, typically, if (i) the output of the photoplethysmograph meets one or more quality criteria and/or (ii) the first estimate meets one or more accuracy criteria, but (iii) the output of the movement sensors does not meet one or more quality criteria and/or (iv) the second estimate does not meet one or more accuracy criteria, the output rate of respiration is typically based on the processed outputs of photoplethysmograph and not the processed measurements of movement, and vice versa.

Processing the output from one or more accelerometers may comprise processing measurements of acceleration parallel to at least two, or at least three (e.g. three) different (typically orthogonal) axes independently to determine a plurality of estimates of the rate of respiration. Processing measurements of acceleration parallel to an axis may comprise carrying out frequency domain analysis of the measurements of acceleration to determine a peak in a frequency spectrum associated with the respiratory cycle. Processing measurements of acceleration parallel to an axis may comprise detecting cardiac cycles within the measurements of acceleration. Processing measurements of acceleration parallel to an axis may comprise detecting respiratory cycle induced variations in a property (e.g. amplitude or intensity) of the measurements of acceleration. The respiratory cycle induced variations may be analysed (e.g. in the frequency domain, for example auto-correlated or processed by Fast Fourier Transform) to determine a respiratory cycle frequency peak, optionally within a predetermined boundary frequency range, for example by determining the most frequent correlation lag observation, or peak frequency component.

The plurality of estimates of the rate of respiration (from the measurements of acceleration parallel to different axes) may be compared. It may be that the processing comprises determining which of the plurality of estimates of the rate of respiration (from the measurements of acceleration parallel to different axes) meet one or more quality criteria and selecting a subset of the plurality of estimates of the rate of respiration (from the measurements of acceleration parallel to different axes) which meet the one or more quality criteria for further processing to determine an output estimate of the rate of respiration. For example, the selected subset of the plurality of estimates of the rate of respiration may be used to determine an average (e.g. an arithmetic or geometric mean, median or mode) rate of respiration (which may be processed further or output as the rate of respiration).

Processing the output from one or more gyroscopes may comprise processing measurements of rate of rotation around at least two, or at least three (e.g. three) different (typically orthogonal) axes independently to determine a plurality of estimates of the rate of respiration (e.g. from the frequency of a peak in the frequency spectrum of a measurement of rotation around a said axis). Processing measurements of rate of rotation around an axis may comprise carrying out frequency domain analysis of the measurements of rate of rotation to determine a peak in a frequency spectrum associated with the respiratory cycle. Processing measurements of rate of rotation around an axis may comprise detecting cardiac cycles within the measurements of rate of rotation. Processing measurement of rate of rotation around an axis may comprise detecting respiratory cycle induced variations in a property (e.g. amplitude or intensity) of the measurements of rate of rotation. The respiratory cycle induced variations may be auto-correlated to determine a frequency peak, optionally within a predetermined boundary frequency range, for example by determining the most frequent correlation lag observation).

The plurality of estimates of the rate of respiration (from the measurements of rate of rotation around the different axes) may be compared. It may be that the processing comprises determining which of the plurality of estimates of the rate of respiration (from the measurements of rate rotation around the different axes) meet one or more quality criteria and selecting a subset of the plurality of estimates of the rate of respiration (from the measurements of rate rotation around different axes) which meet the one or more quality criteria for further processing to determine an output estimate of the rate of respiration. For example, the selected subset of the plurality of estimates of the rate of respiration may be used to determine an average (e.g. an arithmetic or geometric mean, median or mode) rate of respiration (which may be processed further or output as the rate of respiration).

More generally, processing the output from a plurality of movement sensors (e.g. processing the output from one or more accelerometers and/or one or more gyroscopes) may comprise making a plurality of (independent) estimates of the rate of respiration (e.g. by processing the output from each movement sensor independently). For example, the rate of respiration may be estimated from the frequency of a peak in the frequency spectrum of the output from one or more said movement sensors (e.g. an individual movement sensor). A time series of measurements from one or more movement sensors may be analysed to detect cardiac cycles within the time series. One or more respiratory cycle induced variations in a property (e.g. amplitude or intensity) of the measurements may be determined. The respiratory cycle induced variations may be auto-correlated to determine a frequency peak, optionally within a predetermined boundary frequency range, for example by determining the most frequent correlation lag observation).

The said plurality of (independent) estimates may be compared. Processing may comprise determining which of the estimates meet one or more quality criteria and selecting a subset of the plurality of estimates of the rate of respiration which meet the one or more quality criteria for further processing to determine an output estimate of the rate of respiration. For example, the selected subset of the plurality of estimates of the rate of respiration may be used to determine an average (e.g. an arithmetic or geometric mean, median or mode) rate of respiration (which may be processed further or output as the rate of respiration).

It may be that the plurality of movement sensors comprises one or more accelerometers and one or more gyroscopes and in at least some circumstances processing the output from the plurality of movement sensors comprises calculating the output estimate of the rate of respiration from at least one estimate of the rate of respiration obtained from the output of one or more accelerometers and at least one independent estimate of the rate of respiration obtained from the output of one or more gyroscopes.

It may be that the processor is configured to process (and the method may comprise processing) both the output of the at least one movement sensor and the output of the photoplethysmograph to thereby calculate a confidence status representative of a level of confidence in the accuracy of the calculated estimate of the rate of respiration of the subject.

The calculated confidence status is typically selected from a plurality of confidence statuses. The confidence status may have a numerical value.

The output from the processing (carried out by the one or more processors) may for example be to a display, or to memory, or to an input to another algorithm (which may be implemented by the same or different one or more processors).

The monitoring apparatus may comprise a display (or display output) for displaying (or outputting for display), an estimated rate of respiration.

Typically the plurality of confidence statuses includes at least one confidence status (indicative of a relatively low level of confidence) responsive to which no estimate of the rate of respiration is displayed (or output through the display output). Thus, the monitoring apparatus may not display (or output through the display output) an estimate of the current rate of respiration when the level of confidence in the estimate is too low (e.g. below a threshold or otherwise not meeting a confidence requirement).

A further at least two different confidence statuses indicative of different levels of confidence (e.g. a relatively high level of confidence and an intermediate level of confidence) may, in at least some circumstances, be displayed. It may be that both an estimate of the rate of respiration of the subject and data representative of the confidence status are displayed.

It may be that there is at least one confidence status (indicative of a relatively low level of confidence) responsive to which no estimate of the rate of respiration is output (whether displayed, output to a display output or output to any other processor). However, it may be that there is at least one confidence status (indicative of a relatively low level of confidence) responsive to which no estimate of the rate of respiration is displayed (or output to a display output, respectively), but where an estimate of the rate of respiration is calculated and output for further processing. We have found that when confidence in the calculated rate of respiration does not meet a confidence requirement, it is preferable to not display an estimated rate of respiration at all, for example in case it was relied upon when it was not of sufficient accuracy, but it may nevertheless be useful to output the calculated rate of respiration for monitoring or further processing, for example by machine learning algorithms.

It may be that the plurality of confidence statuses includes at least two different confidence statuses indicative of different levels of confidence (e.g. a relatively high level of confidence and an intermediate level of confidence) where in the respective confidence status the monitoring apparatus displays, or output through a display output, both an estimate of the rate of respiration of the subject and data representative of the confidence status. The data representative of the confidence status may be output as a numerical value or as a configuration of a graphical interface (e.g. colour, size or position of a visual element). This enables a physician to know when there is a reduced level of confidence in the estimate of the rate of respiration, while an estimate rate of respiration is displayed.

Therefore, it may be that when the level of confidence in the accuracy of the calculated estimate which fails to meet first confidence criteria (e.g. fails to exceed a threshold) an estimate of the rate of respiration is not displayed. It may be that when the level of confidence in the accuracy of the calculated estimate meets first confidence criteria but fails to meet second confidence criteria, the estimate of the rate of respiration is displayed but one or more signals indicative of limited confidence are also displayed. It may be that when the level of confidence in the accuracy of the calculated estimate meets third confidence criteria the estimate of the rate of respiration is displayed but either one or more signal indicative of a high level of confidence are displayed or one or more signals indicative of limited confidence are not displayed.

The apparatus may comprise a (said) display and be configured to display the estimated rate of respiration on the display. The display may be part of the arm unit.

The photoplethysmograph typically comprises at least one light source configured to generate light in at least two different and typically spaced apart wavelength bands. The PPG typically comprises means to measure the transmission or absorption of light in at least two different and typically spaced apart wavelength bands, for example at least one or at least two photosensors. The PPG data is indicative of the adsorption of light by haemoglobin. The PPG data typically comprises a series of light intensity measurements, or data derived therefrom, indicative of the amount of light at one or more wavelength ranges which has been absorbed by haemoglobin, calibrated for one or one more reference wavelength. Typically, the PPG data comprises light absorption measurements, calculated from light intensity measurements. However, one skilled in the art will appreciate that it is a matter of design implementation what scale is used for the PPG data, whether it increases or decreases with blood volume etc.

By a time series we refer to a sequence of data obtained (typically digitally sampled) at different (and typically equally spaced) times throughout a period of time.

The at least one processor may be integral to the upper arm unit, but this is not required. The at least one processor may be part of one or more separate units, for example an electronic device (such as a mobile telephone and/or internet server) with which the upper arm unit is in electronic communication (for example through at least one wired or wireless interface) and the said determination may be distributed between at least one processor integral to the upper arm unit and at least one processor which is part of one or more separate units. Thus, the processing may take place within the upper arm unit, or remotely from the upper arm unit, or a combination thereof.

The rate of respiration may be expressed in any suitable units, including units proportional to the reciprocal of the rate of respiration, for example numerical estimates of respiratory rate, respiratory frequency, frequency spectra, power spectra etc.

Typically the said processing takes into account time series of measurements from the photoplethysmograph and the one or more movement sensors within a time window. Typically, the time window is at least 20 seconds. Typically, the time window is less than 60 seconds, or less than 40 seconds. Typically, the time window extends up to the time when processing begins. Typically a different (and usually overlapping) time window is analysed periodically (for example, every 1-5 seconds) to provide revised estimates of rate of respiration.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
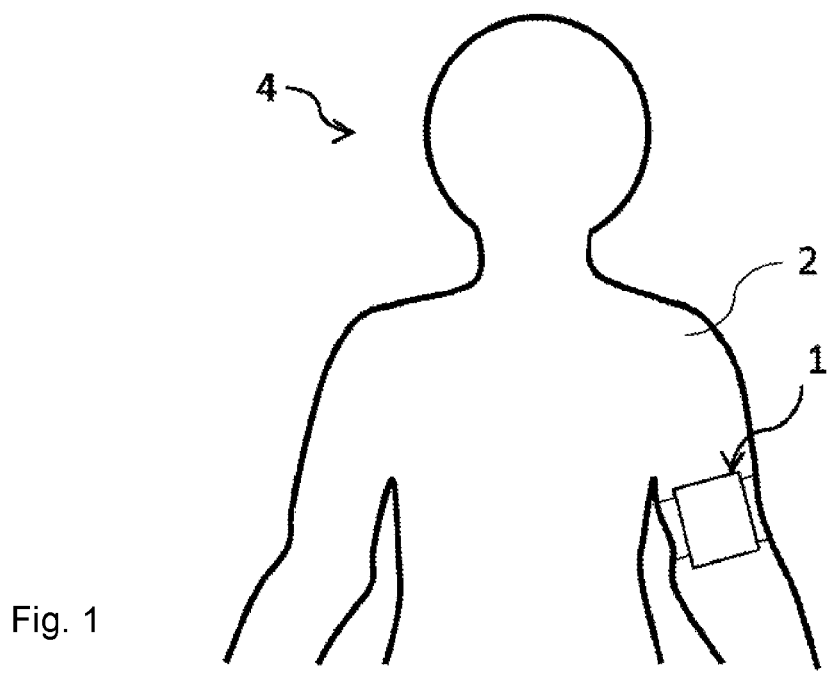
FIG. 1 is a diagram of a subject wearing an ambulatory monitor.
Figure 2:
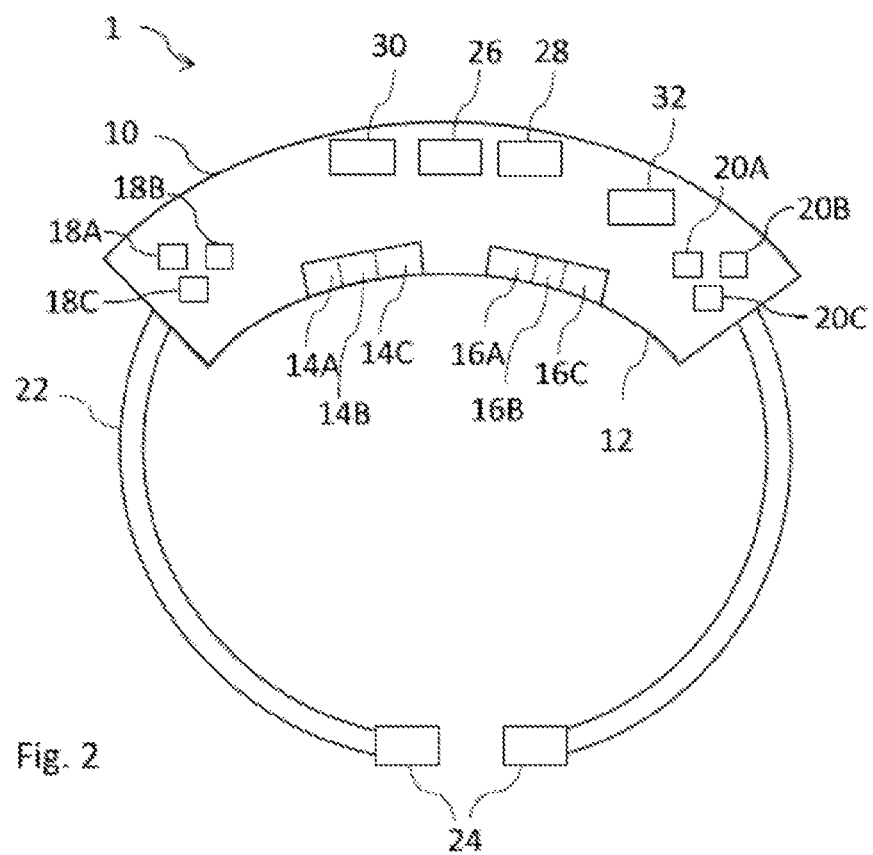
FIG. 2 is a schematic cross section through an ambulatory monitor.

With reference to FIGS. 1 and 2, the invention provides an ambulatory monitor 1, which is fitted to the upper arm 2 of a human subject 4 in use. The monitor is configured to measure the respiratory rate of the subject and typically also a number of other physiological parameters such as the pulse rate and blood pressure of the subject, on an ongoing basis.

The monitor 1 has a casing 10 with an incurvate subject-facing surface 12 on which is mounted a green LED light source 14A, a red LED light source 14B, an infra-red LED light source 14C and first, second and third photosensors 16A, 16B, 16C. The light source and/or photosensors may be on the surface of the casing, underneath the surface of the casing (for example covered by transparent windows) and/or within the body of the casing, in which case they may be connected to the surface of the casing through light guides.

Within the casing there are three accelerometers 18A, 18B, 18C which measure acceleration along three orthogonal axes, typically formed by a three-axis MEMS accelerometer device, and three gyroscopes 20A, 20B, 20C which measure rotation along three orthogonal axes, typically formed by a three-axis solid state gyroscope device. The accelerometers and gyroscopes are fixed in position within the casing with a known orientation. They are calibrated during manufacture. An offset is determined for the gyroscopes so that measurements can be obtained of rotation around an axis in either sense. Accelerometer data is also processed to remove the signal caused by gravity. Further references to accelerometer and gyroscope measurement data refer to the calibrated measurements, after allowing for the gyroscope offset and the subtraction of gravity from the accelerometer signals.

A strap 22 and clasp 24 holds the monitor in place on the patient during use. A microprocessor 26, in electronic communication with memory 28 controls the function of the monitor, including controlling the light source and processing measurements made by the photosensor, accelerometers and gyroscopes. There is also provided an input/output interface 30, including a screen and one or more buttons, and/or a touch screen, or a wired or wireless interface. The device has an integral power supply 32, formed by one or more batteries, and is ambulatory in that a subject may walk around without removing the device or being connected to a monitoring device by a wire.

The LEDs and photosensors, and the associated control electronics and software, together form a photoplethysmograph (PPG). Light from the green LED 14A which is reflected from within the patient's arm is detected by the first photosensor 16 and light from the red and/or infra-red (IR) LED 15B, 15C which is reflected from within the patient's arm is detected by the second photosensor, thereby giving measurements of the reflection of green light and the reflection of red and/or infra-red light. One skilled in the art will appreciate that the first and second photosensors could be replaced by a single photosensor if the green, red and/or IR LEDs are pulsed alternately or otherwise output light signals which are modulated differently such as to enable the reflection of light from the LEDs to be differentiated. The red and IR LEDs and detectors are reference channels and in some embodiments only the red or IR LEDs channels are present.

During operation, a PPG measurement signal is determined from the shallow pulse-rate measurement signal (indicative of reflected green light) and/or a deeper pulse-rate measurement signal (indicative of reflected red or IR light). The PPG measurement signal utilises one or more of the green, red and IR wavelengths, dependent on the pulse-strength of the patient. For example a strong signal may be found with green light at a shallow penetration depth, and this may be the preferred wavelength when a strong signal is available, however, in the case of a subject exhibiting vasoconstriction, a more reliable signal may be found with a red or infra-red light reflected at a deeper penetration depth. The PPG measurement signal is indicative of the blood volume in the patient's tissue adjacent the monitor, in their upper arm. A higher blood volume leads to less reflected light, and vice versa.

The green light used for the measurement signal has a wavelength of 530 nm. The red light used for a reference signal has a wavelength of 660 nm. The IR light used for a reference signal has a wavelength of 950 nm.

The accelerometers provide independent measurements of acceleration parallel to three orthogonal axes and the gyroscopes provide independent measurements of speed of rotation around three orthogonal axes.

Figure 3:
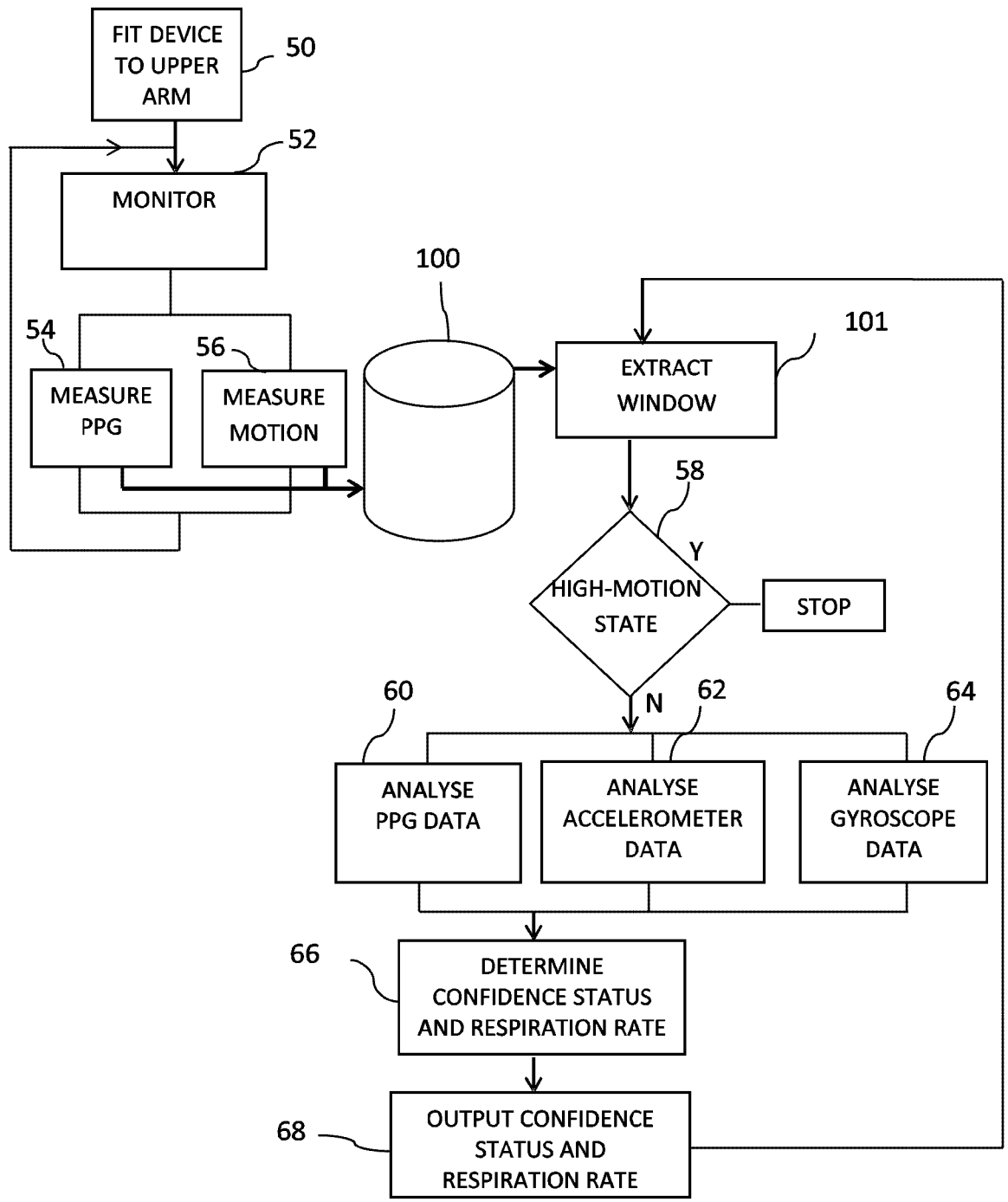
FIG. 3 is a flow chart of an overall process for calculating a respiratory rate.
Figure 4:
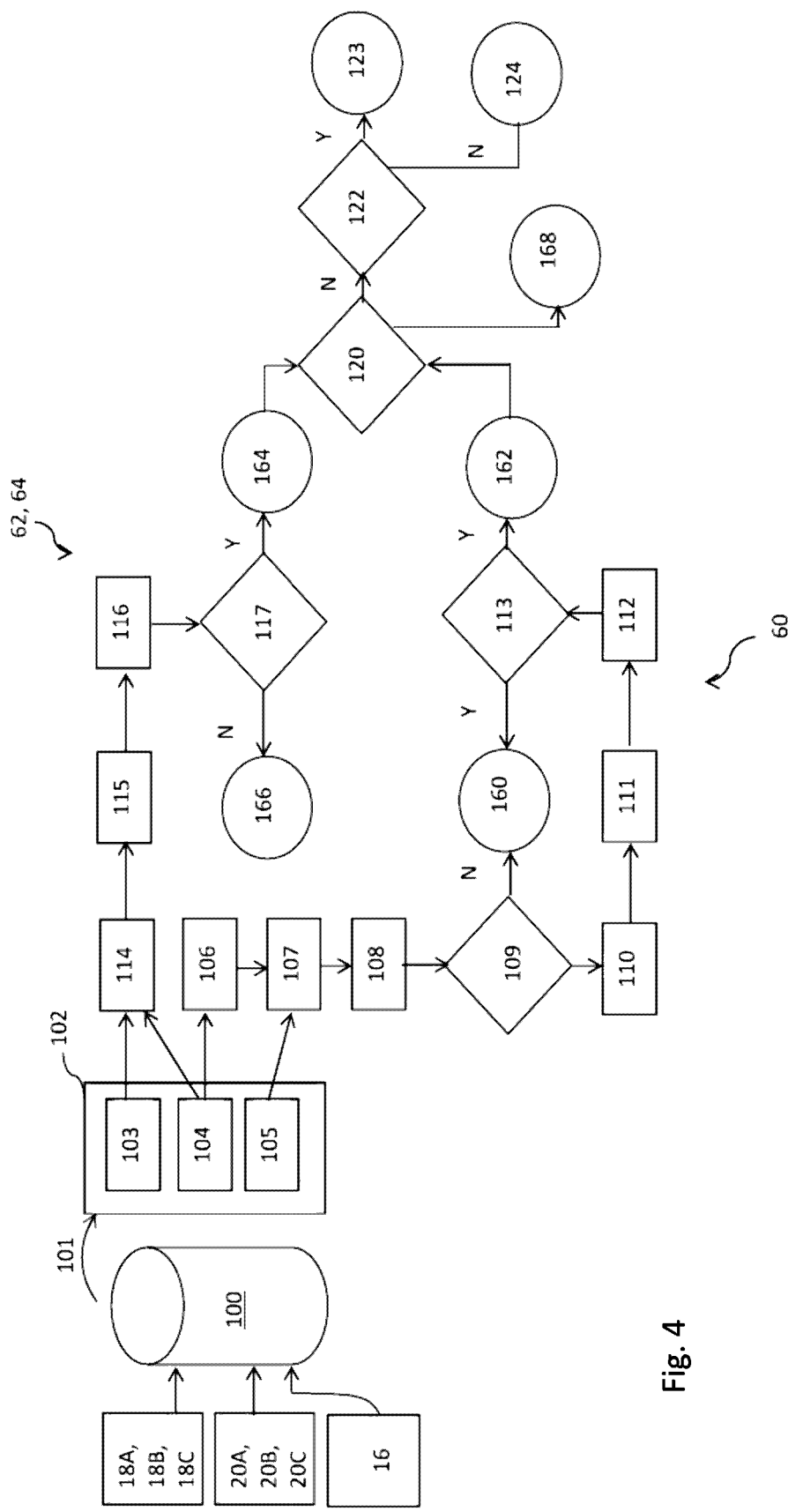
FIG. 4 is a more detailed flow diagram of a process for calculating a respiratory rate.

A procedure for operating the monitor is shown in overview in FIG. 3 and in more detail in FIG. 4. The monitor is fitted 50 to a patient, with the light source and photosensor in direct contact with the patient's skin. Preferably, the monitor is attached to the left arm of the patient although this is not essential and respiratory rate can be determined if the monitor is fitted to the right arm. The monitor typically fits around the bicep muscle. Once the monitor is fitted, monitoring is started 52 and runs continuously until stopped. Monitoring includes both measuring PPG measurement signals 54 from the photoplethysmograph and measuring movement signals 56 from the accelerometers and gyroscopes. These measurements are made periodically and frequently, e.g. at 500 Hz and calculated PPG measurement signals, and measured accelerometer and gyroscope outputs are stored as time series in a data structure 100 in a solid-state memory for subsequent processing.

Periodically, the stored PPG data, accelerometer data and gyroscope data for a window of time is extracted 101 from the database by the processor and processed to determine an estimate of the rate of respiration. In an example, every 2 seconds, a window of data concerning the immediately preceding 24 second period is extracted and processed. A 24 second period is useful in that it will almost always exceed the duration of two consecutive respiratory cycles, enabling the respiratory cycle to be identified and measured, while still providing a current measurement of respiratory rate. Extracting data may include copying it to a different location in memory, or simply identifying start and/or end points where it is stored.

Each window of data is first checked to detect whether the patient is in a high-movement state by detecting whether any of the gyroscope measurements relating to any of the three axes exceeds a threshold. If any of the gyroscope measurements concerning any one of the axes exceeds the threshold (in an example 100 degrees of rotation per second), the apparatus declines to provide an estimate of the rate of respiration. That is because when the patient is in a highly mobile state, it is not practical to reliably obtain a rate of respiration estimate from either the PPG signal or the accelerometer or gyroscope measurements.

Otherwise, as described further below, with reference to FIG. 4, the PPG measurement data is processed 60, the accelerometer data is processed 62 and the gyroscope data is processed 64, to thereby determine independent estimates of the rate of respiration. The processor then determines 66 a confidence status and respiratory rate, which are output 68 through the input/output interface 30, whereupon the analysis process repeats for a further window of data. The output information typically includes a numeric value of the rate of respiration (e.g. number of breaths per minute) and a confidence status is output by displaying an icon indicative of confidence status, colouring the numerical value of the rate of respiration or in some other way.

Turning to FIG. 4, as described above, windows of data are extracted 101 from the stored measurement data 100. The resulting data 102 for a specific window comprises a time series of accelerometer data 103 (measurements of acceleration parallel to each of three axes), a time series of gyroscope data 104 (the velocity of rotation measured around each of three axes) and PPG measurement data 105 (which is indicative of the blood volume). One skilled in the art will appreciate that the units in which these values are expressed is a matter of design choice. In an example, each window relates to 24 seconds of data sampled at 500 Hz, i.e. 12,000 measurement points per sensor.

As described above, a check 106 is made that the subject is not in a high movement state. If they are, then data processing stops and a confidence status 150 is set to a value indicative that no reliable measurement of respiratory rate can be made. No measurement of respiratory rate is output and the display may also show an icon indicating this.

Otherwise, data processing continues. In this description we start with PPG measurement analysis but it does not matter whether PPG measurements or measurements of movement are analysed first, or in parallel.

The window of PPG measurement data 105 is then subject to digital filtering 107 including a fourth order empirically tuned Butterworth band pass filter with a flat passband of 0.2-5 Hz and roll off to avoid entirely removing respiratory frequencies of 0.1 Hz upwards. This retains signals resulting from respiratory cycles with a minimum subject breath-rate of 6 breaths per minute and a maximum subject breath-rate of 40 breaths per minute. A Savitzky-Golay filter is then applied to filter out minor blips caused by the subject twitching.

Figure 5A:
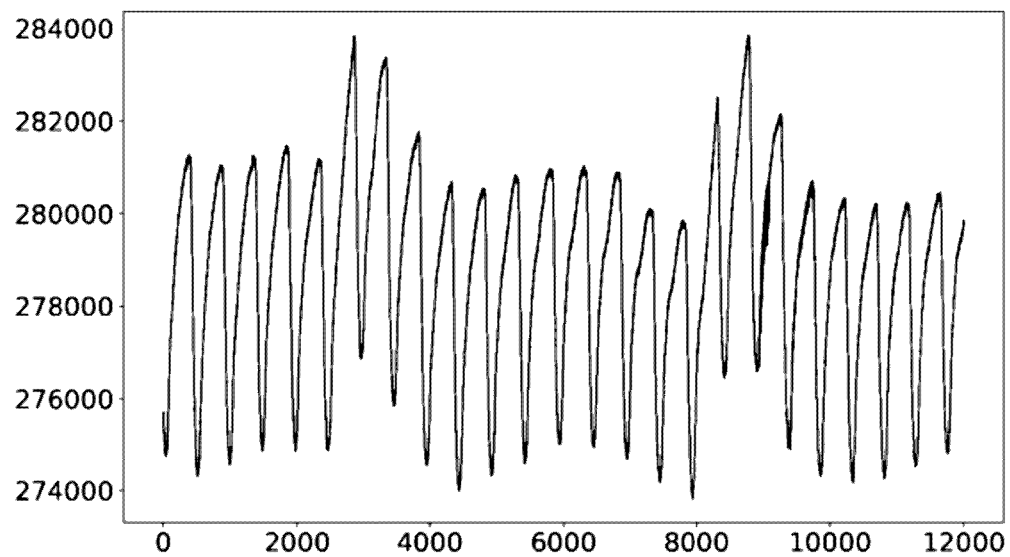
FIG. 5A is an example of a raw PPG measurement signal.
Figure 5B:
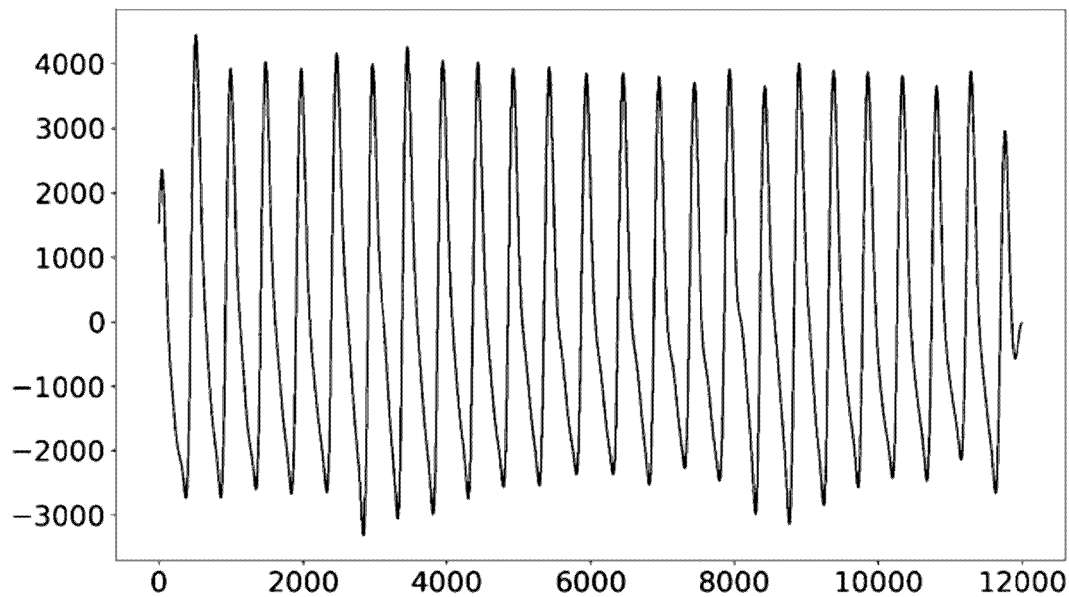
FIG. 5B is the same data after filtering.

This transforms a raw PPG measurement trace such as is shown in FIG. 5A into a filtered trace shown in FIG. 5B. As is known in the art, the individual pulses results from the cardiac cycle and these are modulated by the respiratory cycle which affects the intrapleural pressure, which in turn affects the rate of filling of the right atrium and stroke volume of each cardiac cycle.

In order to model respiratory-induced variations within the pulses, individual cardiac cycles are identified 108, for example major upslopes and their immediately preceding trough and ending peak are identified. This allows the filtered data to be modelled as a plurality of distinct cardiac cycles, illustrated in FIG. 6.

The PPG data is then analysed to determine whether or not a clear signal has been obtained 109. If distinct cardiac cycles cannot be identified, or there are unacceptable gaps (e.g. greater than 200 ms duration) between identified cardiac cycles, these are indicative that the PPG data is not suitable and the PPG analysis procedure stops 160. As discussed below, an estimated respiratory rate may still be output if it can be determined reliably from the accelerometer and/or gyroscope data.

In the next phase, respiratory cycle induced waveforms are extracted for further processing. With reference to FIG.

Figure 7A:
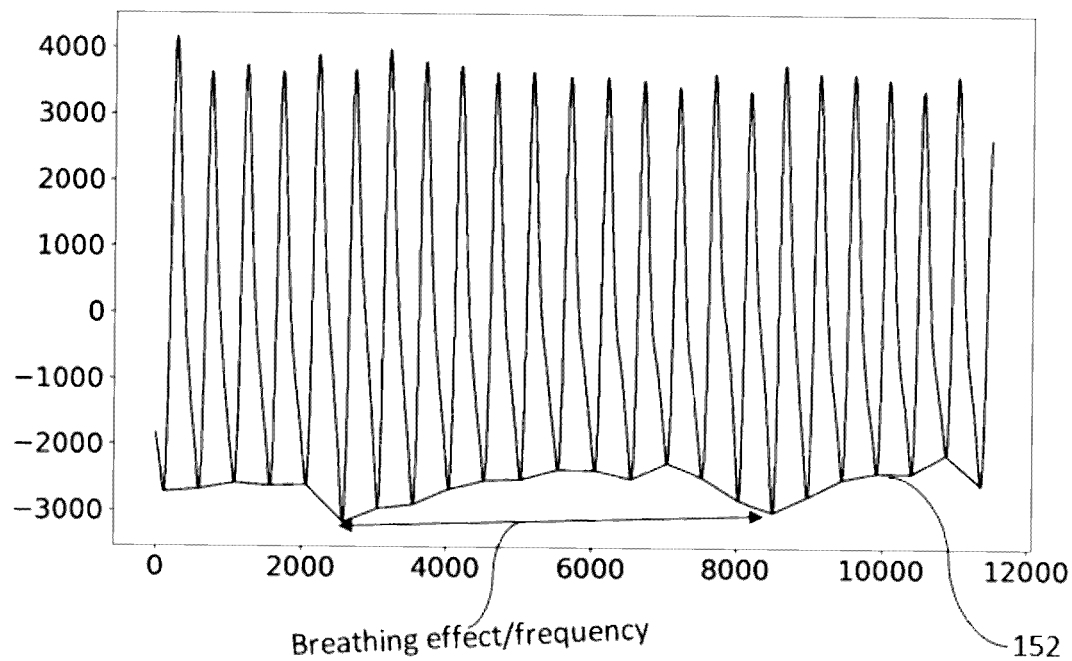
FIG. 7A shows the derivation of a respiratory-induced amplitude variation trace from the PPG signal of FIG. 6.
Figure 7B:
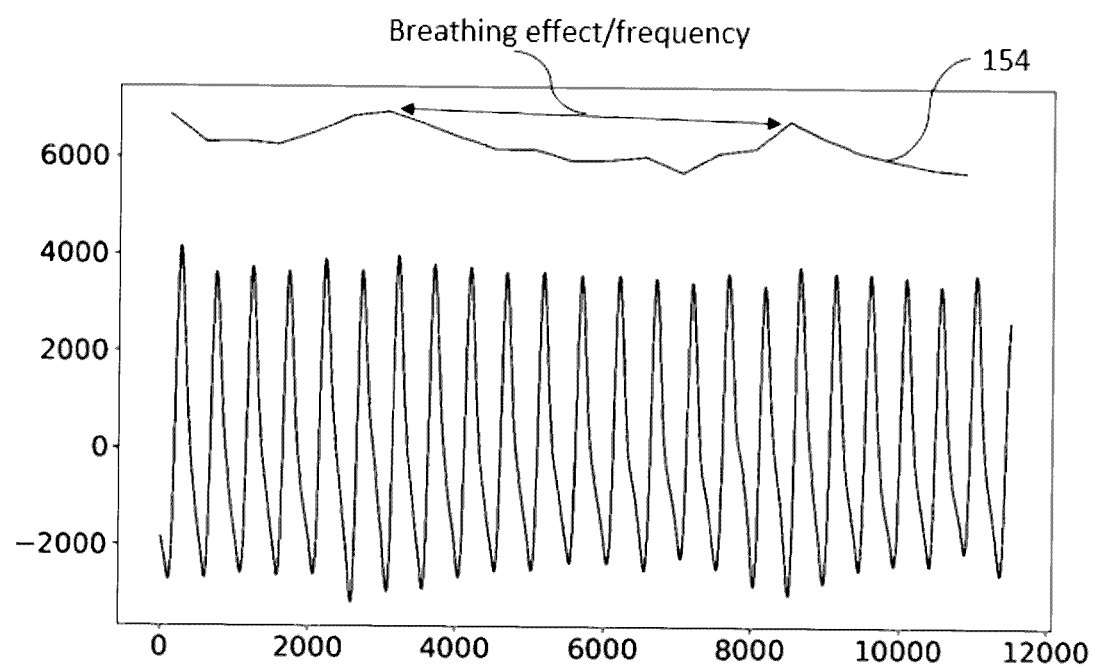
FIG. 7B shows the corresponding respiratory-induced intensity variation.
Figure 7C:
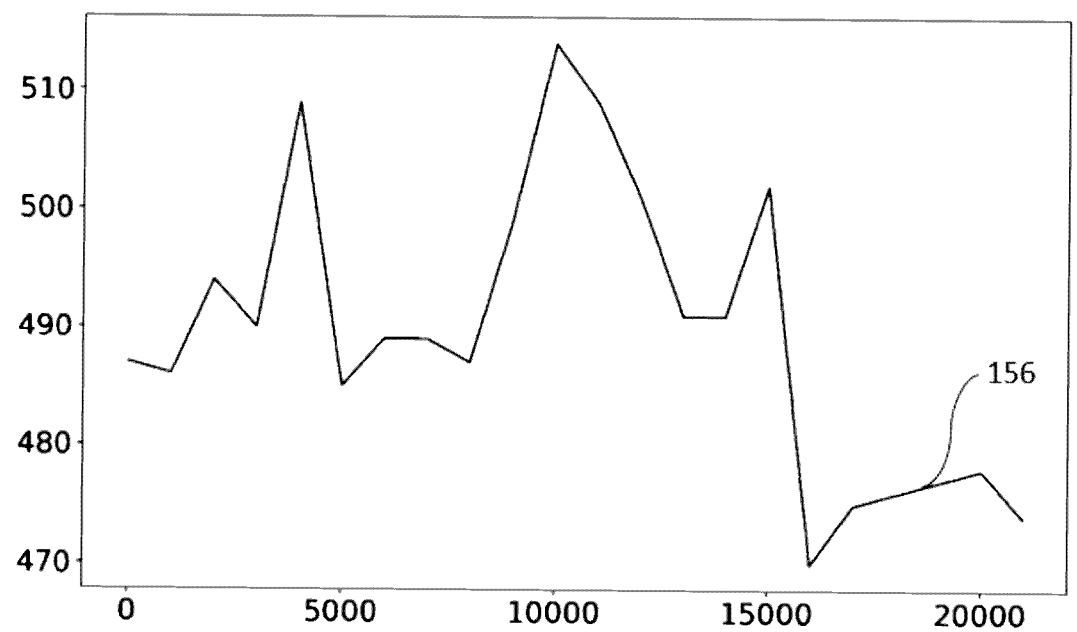
FIG. 7C shows the corresponding respiratory-rate induced frequency variation.

7A, a respiratory-induced amplitude variation 152 trace is determined from the minima (or alternatively maxima) of PPG signal amplitude between individual cardiac cycles. A respiratory cycle induced variation can be clearly seen in FIG. 7A. Similarly, with reference to FIG. 7B, a respiratory-induced intensity variation 154 trace is determined from the maxima (or alternatively minima) of PPG signal intensity (proportional to the difference between the maximum and the minimum of the amplitude). This approach is known from Multiparameter Respiratory Rate Estimation from the Photoplethysmogram (Karlen et al., IEEE Trans Biomed Eng., 2013 July; 60(7): 1946-53), the contents of which are incorporated herein by virtue of this reference. It can be seen that respiratory-cycle induced amplitude and intensity variation traces are substantially cleaner than a corresponding plot of the respiratory-rate induced frequency variation 156 of the individual cardiac cycles shown in FIG. 7C.

Figure 6:
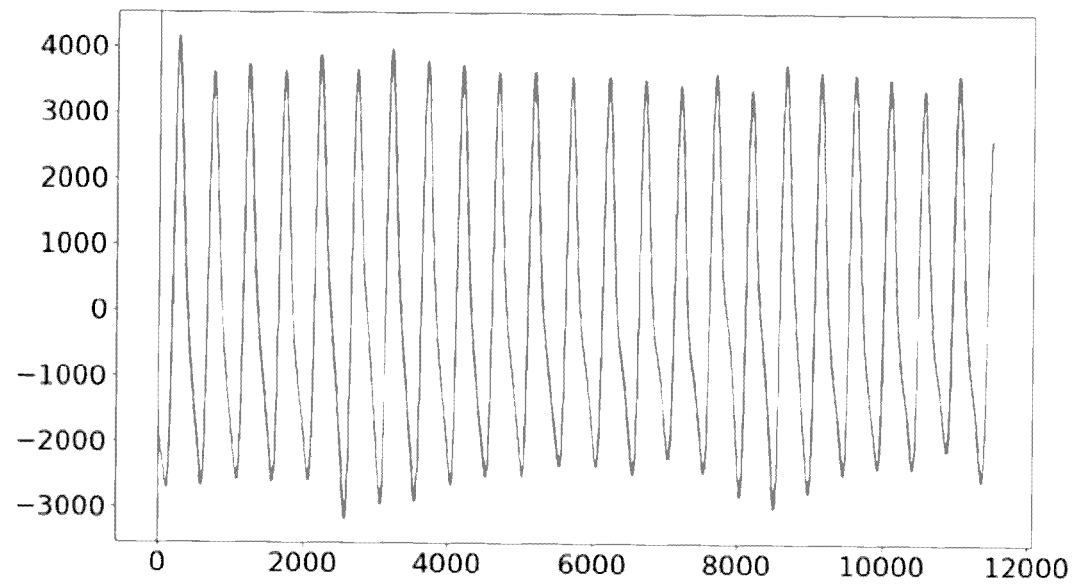
FIG. 6 is the data of FIG. 5B broken down into individual cardiac cycles.
Figure 8A:
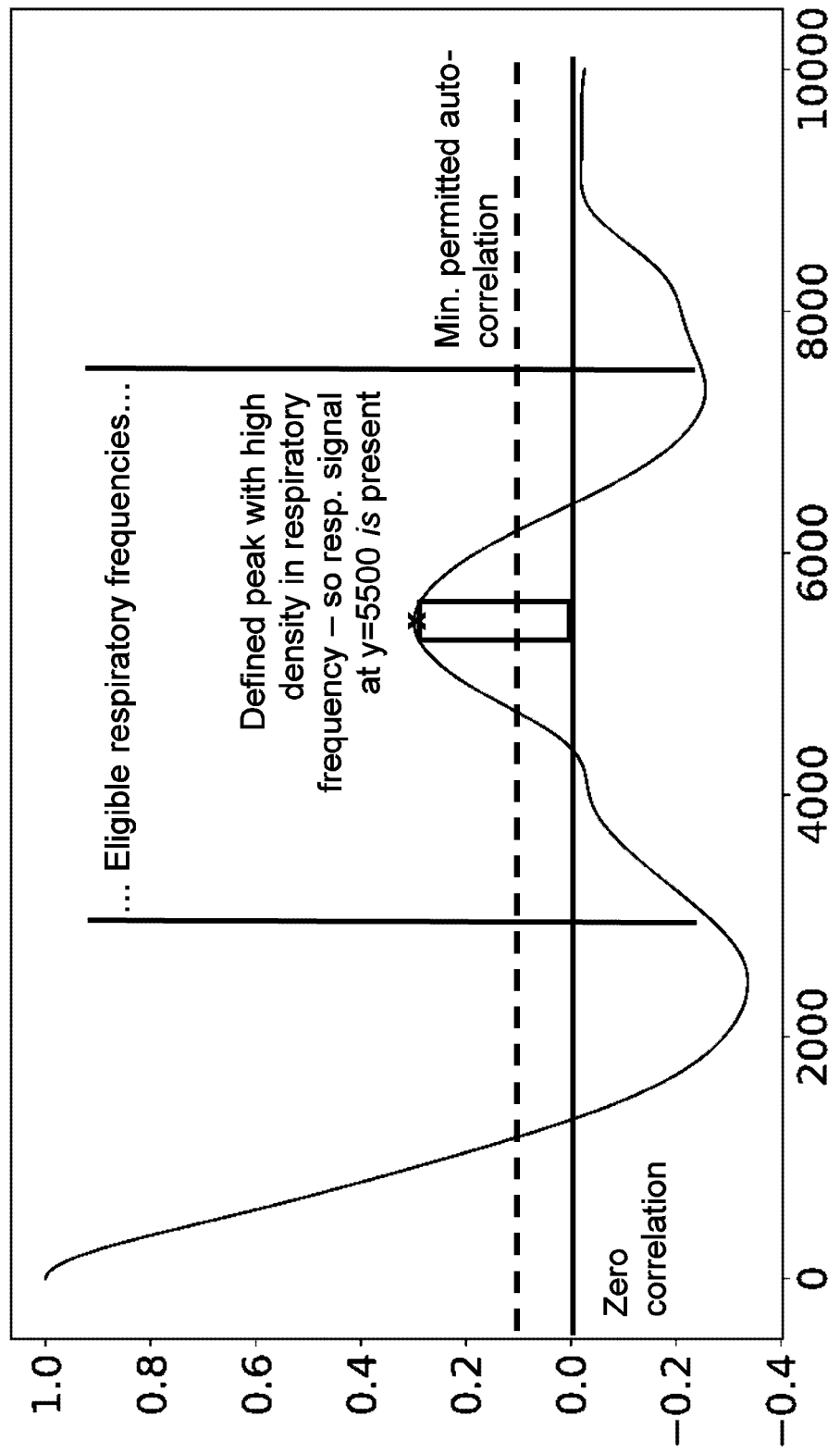
FIGS. 8A, 8B and 8C are the outputs of the auto-correlation function applied to the traces of FIGS. 7A, 7B and 7C respectively.
Figure 8B:
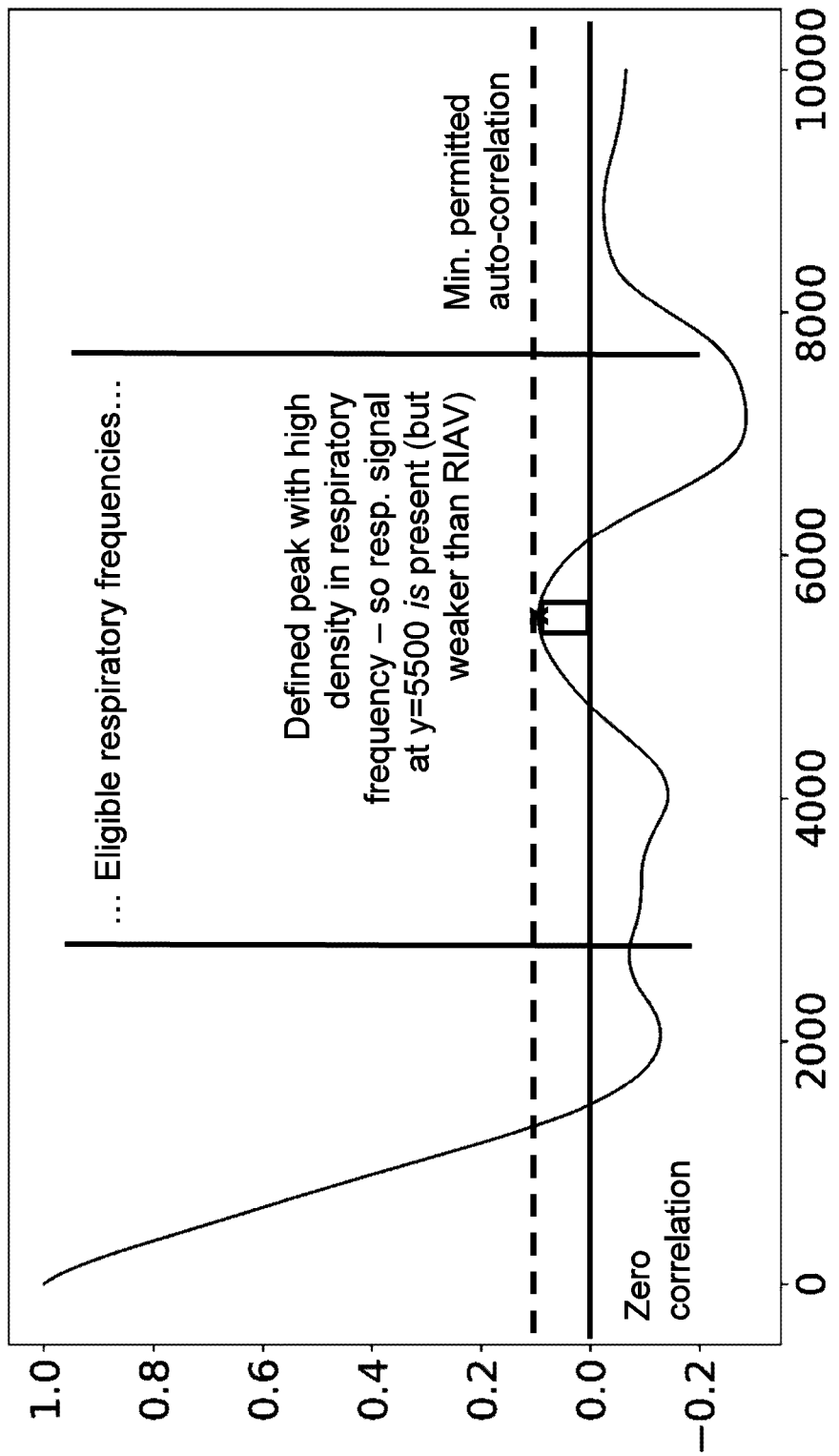
Figure 8C:
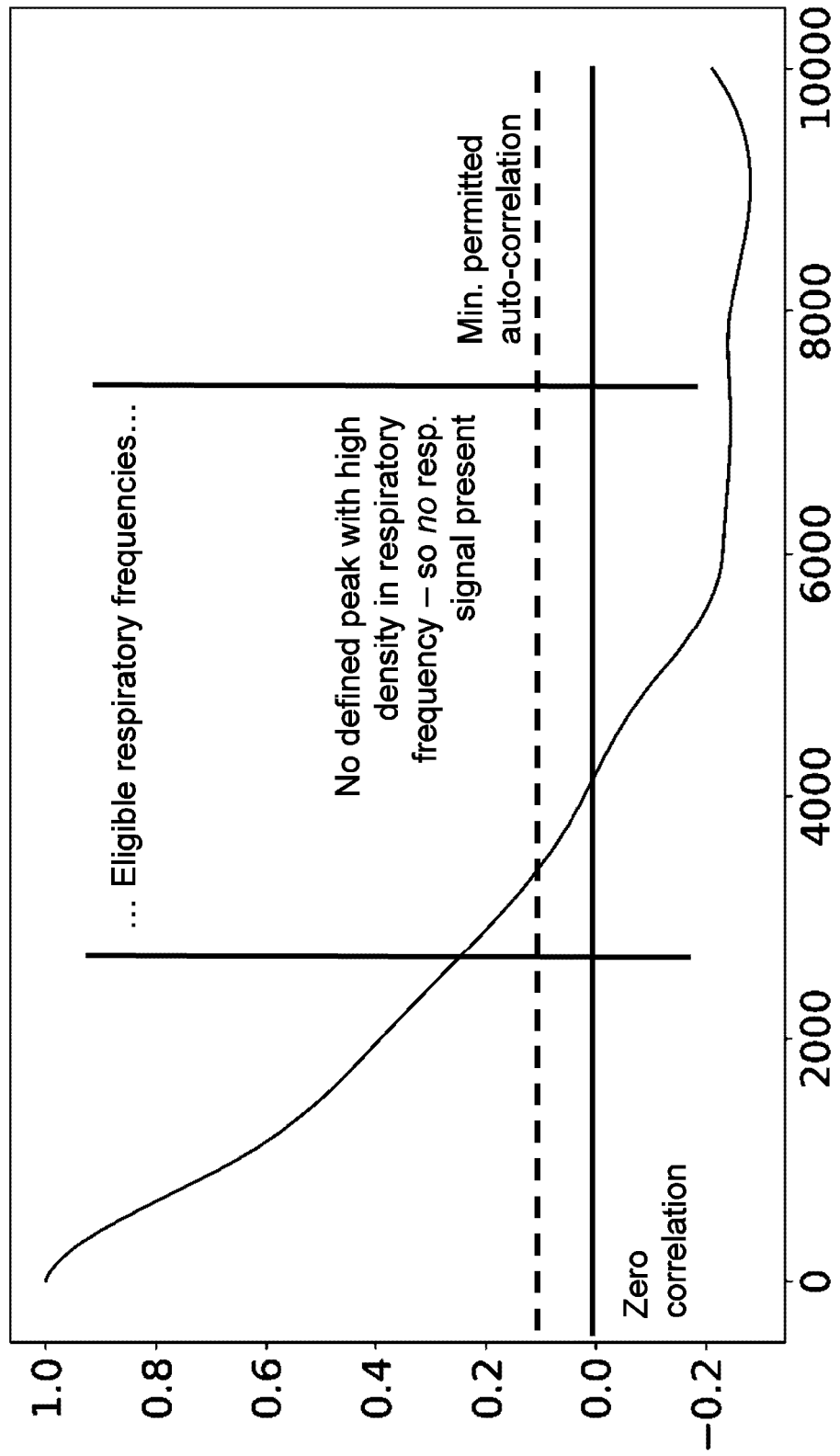

Candidate respiratory frequencies are then identified 112 in the respiratory cycle induced waveforms. The autocorrelation function (which measures the correlation of the waveforms with time-lagged versions of the waveforms and outputs lagged correlation coefficients) is applied to each of the waveforms. The resulting outputs for the data of FIGS. 5 through 7 is shown in FIG. 8A (analysis of respiratory-induced amplitude variation trace 152), 8B (analysis of respiratory-induced intensity variation trace 154), and 8C (analysis of respiratory-induced frequency variation 156).

The lagged correlation coefficients within each of a number of ranges are summed, and expressed as a fraction of the total number of correlation lag observations (referred to herein as the density). A sufficiently high peak in the density (of correlation lag observations), in an eligible frequency range of possible respiration rates, is then identified as a candidate rate of respiration 112. For example, an eligible frequency range may typically be between 6 and 40 bpm, or between 3 and 50 bpm, or between 9 and 30 bpm.

The resulting autocorrelation function data is then further analysed 113 to determine whether the results are of sufficient quality to provide a reliable estimate of the rate of respiration. For the estimate to be found to be reliable, the density (of correlation lag observations) at the frequency of the peak density must be both above a minimum threshold value and a minimum proportion of the total number of correlation lag observations in the eligible frequency range. Furthermore, the frequency of the peak density found by analysing both the respiratory-induced amplitude variation trace 152 and the respiratory-induced intensity variation trace 154 are compared and are required to be within a certain amount of each other. If either of these tests is failed, this is indicative that the PPG data is not suitable and the PPG analysis procedure stops 160. Again, an estimated respiratory rate may still be output if it can be determined reliably from the accelerometer and/or gyroscope data. Provided that the test is met, an estimated rate of respiration derived from PPG measurements 162 is calculated as the mean of the rate indicated by the peak density in the correlation lag observations from the respiratory-induced amplitude variation trace 152 and the respiratory-induced intensity variation trace 154, and output. The confidence status 150 is set to a value indicative of an intermediate level of confidence.

Figure 9:
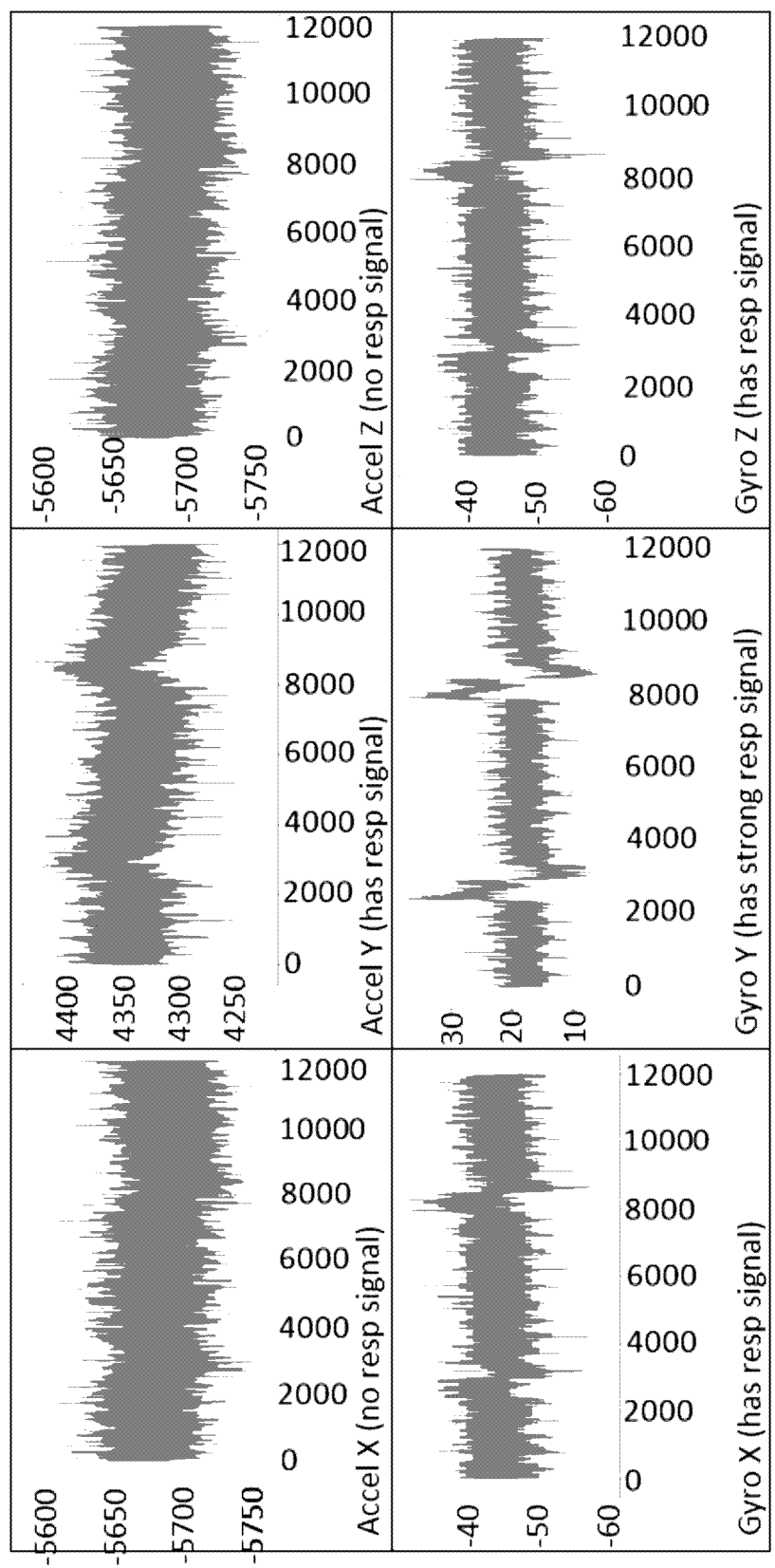
FIG. 9 is a time series of measurements from accelerometers parallel to each of X, Y and Z axes, and gyroscopes parallel to each of X, Y and Z axes.

Turning to the accelerometer and gyroscope measurement data for the measurement window, these are processed independently of the PPG measurement but in generally the same way. The data from each of the 6 available channels (accelerometer data concerning three orthogonal axes and gyroscope data concerning three orthogonal axes) are processed independently. FIG. 9 shows example accelerometer measurement data for each of three axes X, Y, Z and gyroscope data for each of three axes X, Y, Z. In this example, there is a respiratory signal discernible in the accelerometer Y axis data but the not the accelerometer X axis or Z axis data and there is a respiratory signal discernible in the gyroscope X and Z data and a strong respiratory signal discernible in the gyroscope Y data. The axes in which signals can be identified depend on the posture and/or movement pattern of the subject at the time in question.

First, after basic filtering, individual cardiac cycles are identified 114 in the signals from each of the 6 traces. Then respiratory cycle induced amplitude variation traces are formed 115 from each of the 6 traces, for example, by connecting the maximum or minimum measurement of each consecutive cardiac cycle peak of amplitude.

Figure 10:
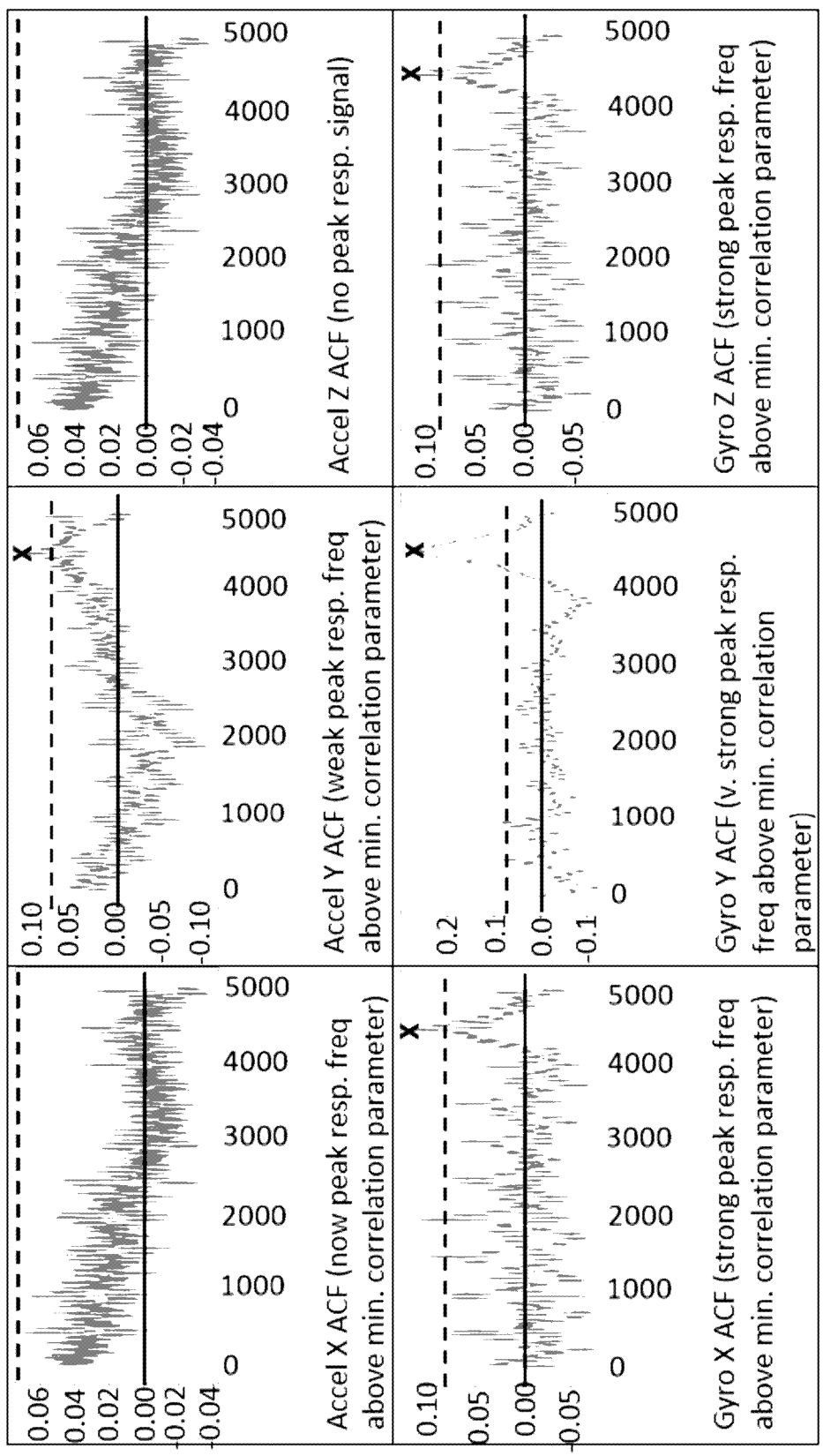
FIG. 10 is plots of the density of auto-correlation lag observations in respiratory-rate induced amplitude variation traces derived from the time series of FIG. 9, focussed in on an eligible range of possible respiratory frequencies.

Again, the autocorrelation function is applied to each respiratory cycle induced trace and the density (numerical fraction) of autocorrelation lag observations within each of a range of frequency bands is calculated. The resulting data is shown in FIG. 10 for each of the 6 traces of FIG. 9. FIG. 10 shows only values for an eligible frequency range (of possible respiratory rate frequencies) shown on the y-axis.

Peaks in the density of autocorrelation lag observations are identified and validated 117 by determining whether they are above a minimum value and whether they are a sufficiently high fraction of total observations with the eligible frequency range. In the data shown in FIG. 11, a peak respiratory frequency above a minimum density can be identified in each of the accelerometer X-axis and Y-axis data, but not the Z-axis data which does not have a clear peak. Strong peaks in the density of autocorrelation lag observations are found for the gyroscope X-axis and Z-axis data and there is a very strong peak in the gyroscope Y-axis data.

The peaks identified from each axis of each of the accelerometer and gyroscope data are compared as part of the validation procedure and if there are several which give a sufficiently similar value for the peak respiratory frequency that is stored as a movement-derived estimate 164 of the respiratory rate. For example, it may be that if 3 of the 6 data sets give a respiratory rate of within 2 breaths per minute, it is determined that a reliable respiratory rate has been identified and an average of those measurements is selected as the movement-derived estimate of the respiratory rate, and the confidence status is set to a value indicative of an intermediate level of confidence. If there are not a sufficient number of sufficiently similar peak frequencies, no movement-based respiratory rate signal is determined 166, and the confidence status is set to a value indicative that no reliable movement-derived estimate of the respiratory rate has been identified.

It is then determined 120 whether estimates of the rate of respiration 162, 164 have been obtained from both PPG-derived and the movement-derived calculations respectively.

If a rate of respiration has been estimated by only one of these routes, that rate of respiration is selected at the output estimate of the current rate of respiration 168 and that is output. The confidence status 150 is set to a value indicative of an intermediate level of confidence in the rate of respiration, because although a value has been derived with reasonable confidence, it is derived only from frequency analysis of one of the two types of measurement data.

However, if a rate of respiration has been estimated by both of these routes, then it is checked 22 that the difference between them is within a threshold (e.g. a maximum of 3 breaths per minute, or 20% etc.) and provided that that test is met, a respiratory rate estimate is output 170 and the confidence status 150 is set to a value indicative of a high confidence in the rate of respiration, because it has been validated by analysing two different types of data (PPG and movement). The output respiratory rate may be the average (e.g. arithmetic or geometrical mean) of the two estimated respiratory rates.

On the other hand, if the difference between the two calculated rates of respiration is not within the threshold, then no estimate of respiratory rate is output and the confidence status 150 is set to a value indicative that a sufficiently accurate respiratory rate could not be established.

Accordingly, the invention calculates a rate of respiration taking two different types of measurement, PPG measurements and measurements of movement, made with an upper arm mounted wearable monitor. We have found that the results are reliable, the circumstances in which an accurate estimate of the rate of respiration cannot be obtained are minimised and false estimates of the rate of respiration are suppressed. This is especially helpful in the case of monitoring services (including remote monitoring services and/or devices which generate alerts or alarms) where it is important to be able to estimate a rate of respiration for as high a proportion of the time as possible, but where even short period of false readings could generate incorrect alarms or alerts. Medical practitioners and monitoring services are informed of the level of confidence of the estimated rate of respiration and can take this into account when making decisions.

Nevertheless, in some embodiments, if an insufficient level of accuracy is obtained then the apparatus does not display the estimated rate of respiration where it may be viewed by medical personnel treating or caring for the subject but continues to log the estimated rate of respiration, or to output it to other apparatus, such as monitoring apparatus or to process the estimated rate of respiration, typically along with other parameters, for example using machine learning algorithms, for further diagnostic purposes. Machine learning algorithms can sometimes determine reliable data by combining a relatively unreliable data source with additional data sources.

Furthermore, the device is tolerant of a certain amount of movement—and if there is too much movement will decline to provide a wrong estimate—and can provide respiratory rate measurements using the movement sensors even where PPG signals are unreliable due to vasoconstriction.

Although in this example embodiment, the data processing and calculation of the rate of respiration is carried out in the monitor, it may be carried out wholly or in part elsewhere. For example, measured digitised PPG data, accelerometer data and gyroscope data may be transmitted wirelessly to a recipient data processing device such as a mobile telephone, or other personal computing device, or server (through the internet), and subsequent data processing may be carried out on the recipient data processing device. The calculated rate of respiration may then be displayed on the recipient data processing device (e.g. the screen of a mobile telephone), transmitted back to the monitor for display, or to another recipient (e.g. an electronic device in the possession of a medical professional or a monitoring service etc.)

In some embodiments, the rate of respiration is calculated remotely by a server and transmitted back to the monitor or a portable electronic device for display locally to the subject, or to personnel treating or caring for the subject, only when the rate of respiration has been calculated with sufficient accuracy, but the server, or other processors continue to process the rate of respiration for data logging or other diagnostic purposes.

The invention claimed is:

1. A method of measuring the respiratory rate of a subject using an upper arm unit which is attached to a subject's upper arm, the upper arm unit comprising at least one movement sensor and an photoplethysmograph configured to monitor blood volume within the subject's upper arm while the upper arm unit is worn on the subject's upper arm, the method comprising processing both the output of the at least one movement sensor and the output of the photoplethysmograph to thereby calculate an estimate of the rate of respiration of the subject, and then outputting the calculated estimate of the rate of respiration of the subject, wherein processing the output of the at least one movement sensor comprises detecting respiratory movement of the thorax using the at least one movement sensor within the upper arm unit.

2. A method according to claim 1, wherein the processing comprises calculating at least one first estimate of the rate of respiration by determining the frequency of a respiratory cycle induced variation in the output of the photoplethysmograph, and at least one second estimate of the rate of respiration by determining the frequency of a respiratory cycle induced variation in the output of the at least one movement sensor.

3. The method according to claim 1, wherein the at least one movement sensor is only positioned on the upper arm.

4. Monitoring apparatus for measuring the respiratory rate of a subject, the monitoring apparatus comprising an upper arm unit configured for attachment to a subject's upper arm, the upper arm unit comprising at least one movement sensor and a photoplethysmograph (PPG) configured to a monitor blood volume within the subject's upper arm while the upper arm unit is worn on the subject's upper arm, at least one processor programmed to process both the output of the at least one movement sensor and the output of the photoplethysmograph to thereby calculate and output an estimate of the rate of respiration of the subject, (a) a first estimate of the rate of respiration calculated by determining the frequency of a respiratory cycle induced variation in the output of the photoplethysmograph; or (b) a second estimate of the rate of respiration calculated by determining the frequency of a respiratory cycle induced variation in the output of the at least one movement sensor, and wherein the second estimate of the rate of respiration is the estimated respiratory rate induced variation in the output of the at least one movement sensor within the upper arm unit.

5. Monitoring apparatus according to claim 4, wherein the upper arm unit comprises a housing which includes the at least one movement sensor and the photoplethysmograph therein.

6. Monitoring apparatus according to claim 5, wherein the processor is further configured to perform processing that comprises analysing whether the output from the photoplethysmograph meets one or more quality criteria.

7. Monitoring apparatus according to claim 4, wherein the processor is further configured to perform processing of the output from the at least one movement sensor the processing comprising analysing a time series of measurements from the at least one movement sensors to detect cardiac cycles within the time series.

8. Monitoring apparatus according to claim 7, wherein one or more respiratory cycle induced variations in a property of the measurements is determined.

9. Monitoring apparatus according to claim 4, wherein the processor is further configured to perform processing comprising both:
   (a) calculating at least one of first estimate of the rate of respiration by determining the frequency of the respiratory cycle induced variation in the output of the photoplethysmograph; and
   (b) calculating at least one of the second estimate of the rate of respiration by determining the frequency of the respiratory cycle induced variation in the output of the at least one movement sensor.

10. Monitoring apparatus according to claim 4, wherein the at least one movement sensor comprises one or more accelerometers and one or more gyroscopes, and wherein a plurality of the second estimates of the rate of respiration are calculated from measurements of acceleration parallel to different axes and compared and/or a plurality of the second estimates of the rate of respiration are calculated from measurements of the rate of rotation around different axes and compared.

11. Monitoring apparatus according to claim 4, wherein the processor is further configured to perform processing which comprises determining which of the estimates of the rate of respiration meet one or more quality criteria and selecting a subset of the plurality of the estimates of the rate of respiration which meet the one or more quality criteria for further processing to determine an output estimate of the rate of respiration.

12. Monitoring apparatus according to claim 4, wherein the upper arm unit comprises a housing having an incurvate subject-facing surface, including a light transmitting surface.

13. Monitoring apparatus according to claim 4, wherein the processor is further configured to process both the output of the at least one movement sensor and the output of the photoplethysmograph to thereby calculate a confidence status representative of a level of confidence in the accuracy of the estimate of the rate of respiration of the subject.

14. Monitoring apparatus according to claim 13, further comprising a display, wherein the calculated confidence status is selected from a plurality of confidence statuses, the plurality of confidence statuses includes at least one confidence status responsive to which no estimate of the rate of respiration is displayed, and at least two different confidence statuses indicative of different levels of confidence wherein the monitoring apparatus displays both estimate of the rate of respiration of the subject and data representative of the confidence status.

15. Monitoring apparatus according to claim 13, wherein the monitoring apparatus comprises a display or a display output, for displaying, or outputting for display, the estimate of the rate of respiration and wherein the monitoring apparatus does not display or output to the display output, an estimate of the current rate of respiration when the level of confidence in the accuracy of the calculated estimate of the rate of respiration of the subject does not meet a confidence requirement.

16. Monitoring apparatus according to claim 4, wherein the processor is configured to output either:
   (a) the first estimate of the rate of respiration calculated by determining the frequency of the respiratory cycle induced variation in the output of the photoplethysmograph; or
   (b) the second estimate of the rate of respiration calculated by determining the frequency of the respiratory cycle induced variation in the output of the at least one movement sensor,
   in dependence on (i) whether the output of the photoplethysmograph meets one or more quality criteria and/or (ii) whether the first estimate meets one or more accuracy criteria; and also (iii) whether the output of the at last one movement sensor meets one or more quality criteria and/or (iv) whether the second estimate meets one or more accuracy criteria.

17. Monitoring apparatus according to claim 4, wherein the processor is further configured to output a rate of respiration calculated from both as least one of the first estimate of the rate of respiration calculated by determining the frequency of the respiratory cycle induced variation in the output of the photoplethysmography; and at least one of the second estimate of the rate of respiration calculated by determining the frequency of the respiratory cycle induced variation in the output of the at least one movement sensor.

18. Monitoring apparatus according to claim 17, wherein the processor is further configured to output a rate of respiration calculated from both the at least one of the first estimate of the rate of respiration and the at least one of the second estimate of the rate of respiration if both the at least one said first estimate and the at least one said second estimate meet at least one similarity criterion.

19. Monitoring apparatus according to wherein the at least one movement sensor comprises one or more gyroscopes to thereby detect rotational movement along at least two axes.

20. Monitoring apparatus according to claim 4, wherein none of the at least one movement sensor is configured to be on the thorax.

21. A method of measuring the respiratory rate of a subject using an upper arm unit which is attached to a subject's upper arm,
   the upper arm unit comprising at least one movement sensor and an photoplethysmograph configured to monitor blood volume within the subject's upper arm while the upper arm unit is worn on the subject's upper arm,
   the method comprising processing both the output of the at least one movement sensor and the output of the photoplethysmograph to thereby calculate an estimate of the rate of respiration of the subject, and then outputting the calculated estimate of the rate of respiration of the subject, and
   wherein the at least one movement sensor is only positioned on the upper arm.

* * * * *